(12) United States Patent
Rogers et al.

(10) Patent No.: US 9,259,230 B2
(45) Date of Patent: Feb. 16, 2016

(54) MICROFRACTURE PICK

(71) Applicant: Smith & Nephew, Inc., Memphis, TN (US)

(72) Inventors: Jon-Paul Rogers, North Smithfield, RI (US); Timothy P. Callahan, Attleboro, MA (US); Paul O'Connor, Norfolk, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/444,395

(22) Filed: Jul. 28, 2014

(65) Prior Publication Data

US 2014/0336656 A1 Nov. 13, 2014

Related U.S. Application Data

(63) Continuation-in-part of application No. PCT/US2013/021400, filed on Jan. 14, 2013, which is a continuation of application No. PCT/US2014/022537, filed on Mar. 10, 2014.

(60) Provisional application No. 61/591,980, filed on Jan. 29, 2012, provisional application No. 61/781,215, filed on Mar. 14, 2013.

(51) Int. Cl.
*A61B 17/16* (2006.01)
*A61B 17/00* (2006.01)

(52) U.S. Cl.
CPC ... *A61B 17/1604* (2013.01); *A61B 2017/00477* (2013.01)

(58) Field of Classification Search
CPC .................................. A61B 17/1604
USPC .......................................... 606/184, 185, 190
See application file for complete search history.

(56) References Cited

U.S. PATENT DOCUMENTS

| | | | | |
|---|---|---|---|---|
| 4,239,045 A * | 12/1980 | Schlein | ......................... | 606/83 |
| 4,583,270 A * | 4/1986 | Kenna | ........................ | 407/29.15 |
| 5,713,906 A * | 2/1998 | Grothues-Spork et al. | ..... | 606/99 |
| 6,764,491 B2 * | 7/2004 | Frey et al. | ....................... | 606/85 |
| 8,840,622 B1 * | 9/2014 | Vellido et al. | ................... | 606/99 |
| 2007/0270870 A1 * | 11/2007 | Torrie et al. | ..................... | 606/86 |

(Continued)

FOREIGN PATENT DOCUMENTS

WO 2007106895 A2 9/2007

OTHER PUBLICATIONS

International Search Report, PCT/US2014/022537, dated May 27, 2014.

*Primary Examiner* — David Bates
(74) *Attorney, Agent, or Firm* — Burns & Levinson LLP; Joseph M. Maraia

(57) ABSTRACT

A microfracture pick having features configured to aid a user in advancing the microfracture pick through bone. The microfracture pick has an elongated member with a proximal end, a distal end, a sharp, optionally angled tip disposed adjacent the distal end of the elongated member, and at least one engaging feature disposed at one or more locations on the elongated member for engaging a complementary feature of a strike instrument. By striking an impact surface of the strike instrument, the user can produce a force that is translated via the elongated member of the microfracture pick through the tip, thereby making penetration of the tip through the bone more effective.

4 Claims, 18 Drawing Sheets

(56) References Cited

U.S. PATENT DOCUMENTS

| | | | |
|---|---|---|---|
| 2009/0143782 A1* | 6/2009 | Levi | 606/79 |
| 2010/0331851 A1* | 12/2010 | Huene | 606/100 |
| 2010/0331897 A1* | 12/2010 | Lindner | 606/305 |
| 2012/0071876 A1 | 3/2012 | Stoll et al. | |
| 2012/0290020 A1* | 11/2012 | Meridew | 606/86 R |
| 2013/0053904 A1* | 2/2013 | Penenberg | 606/86 R |

* cited by examiner

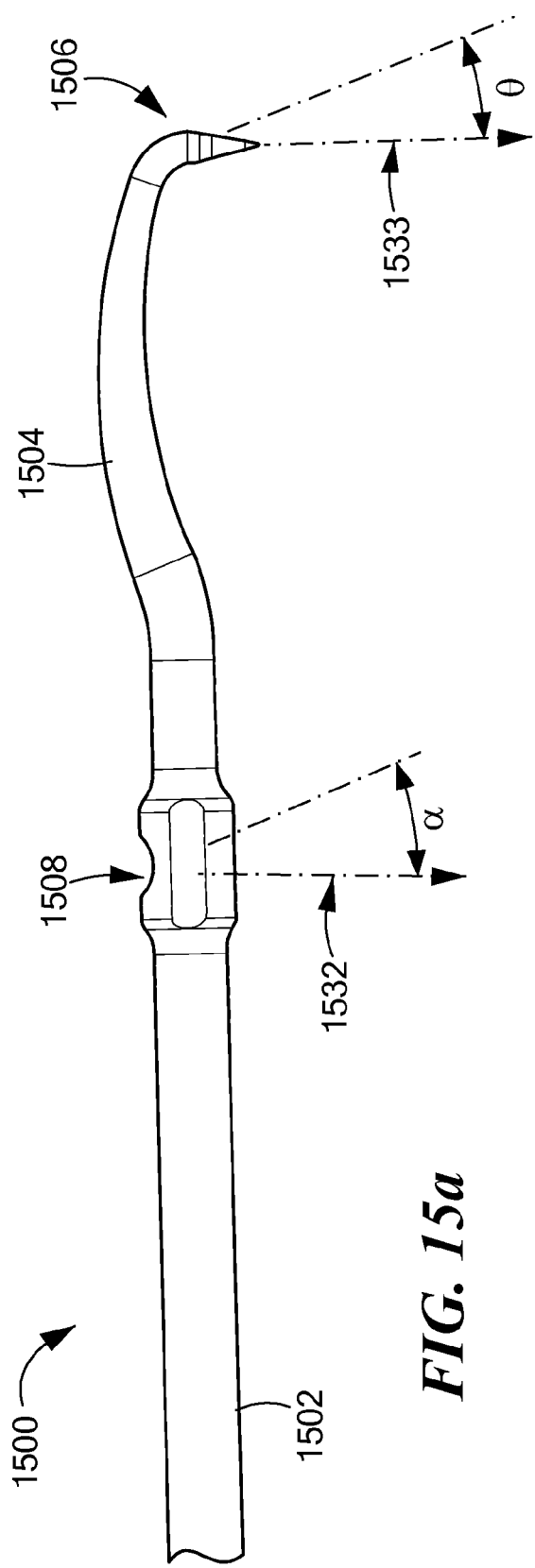
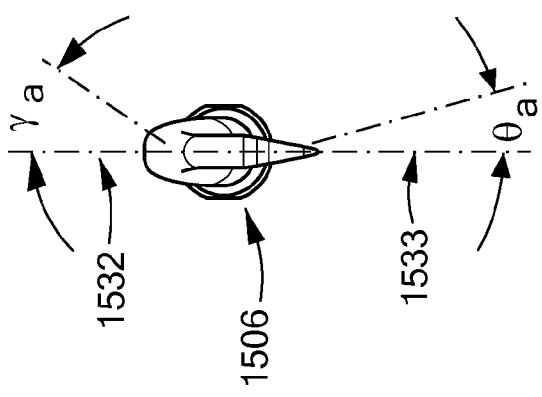
FIG. 15a
FIG. 15b

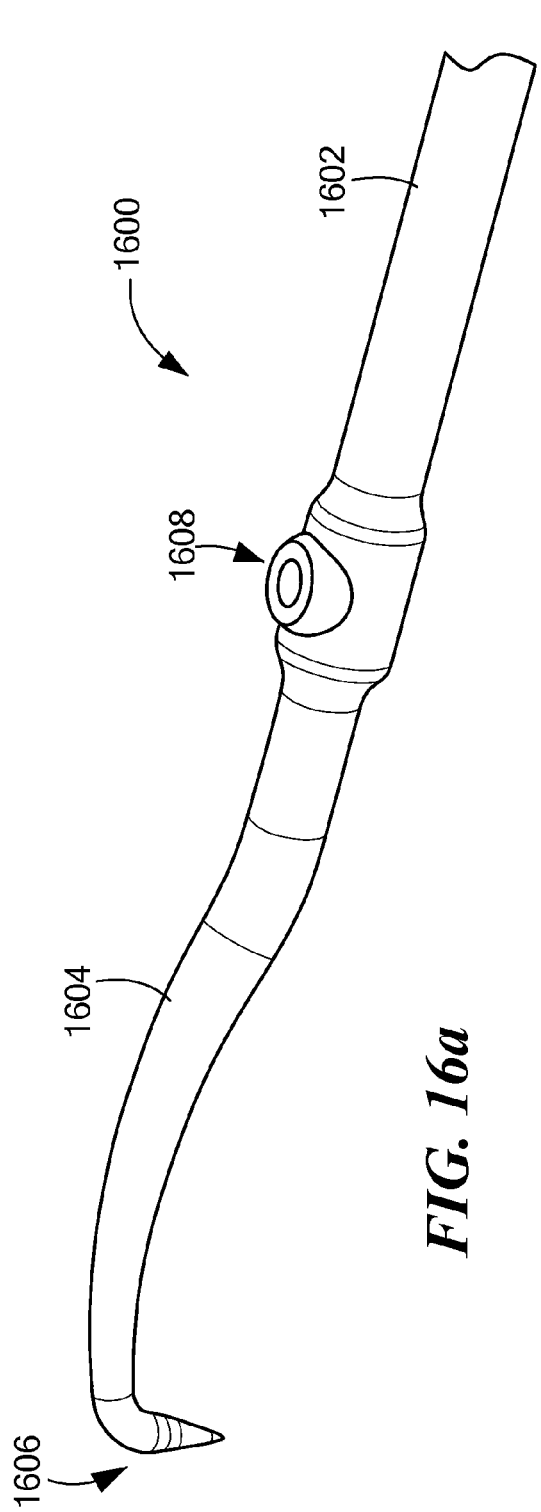
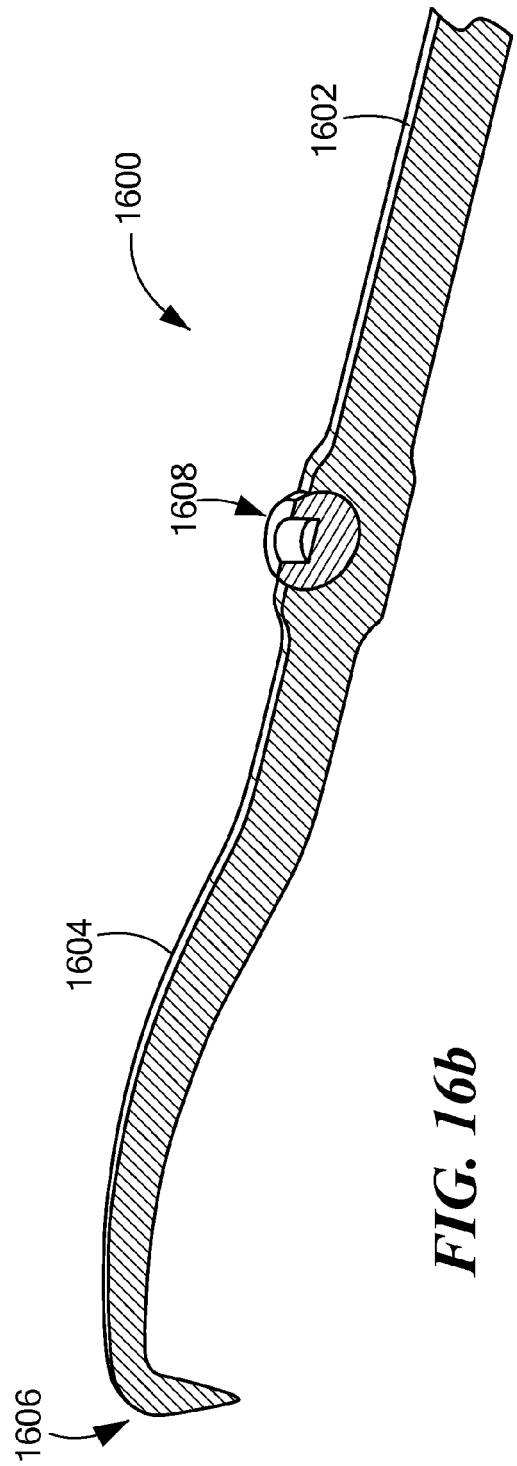
FIG. 16a
FIG. 16b

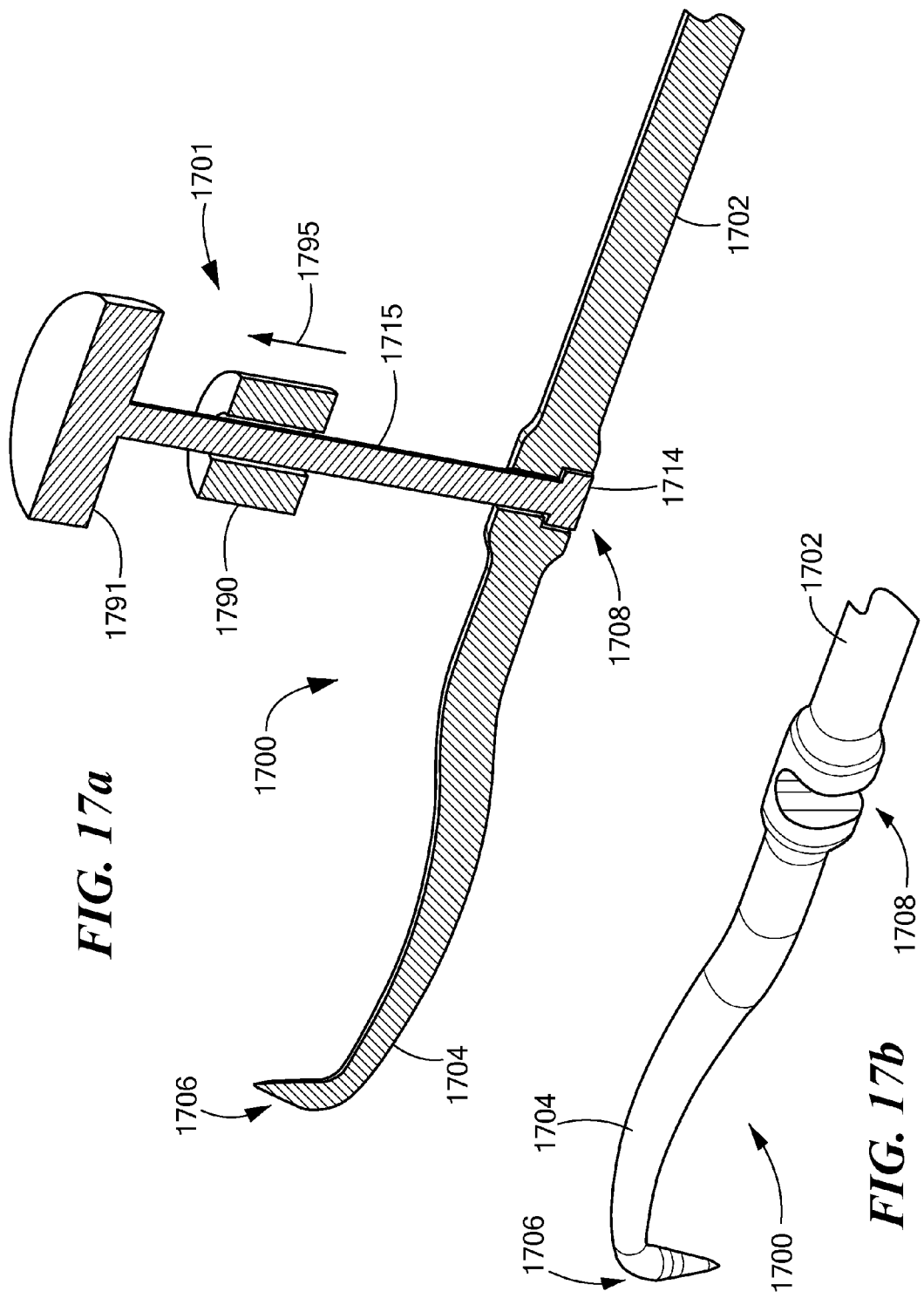

MICROFRACTURE PICK

CROSS REFERENCE TO RELATED APPLICATIONS

This application is a continuation in part of the International Application No. PCT/US2013/021400 filed Jan. 14, 2013 entitled MICROFRACTURE PICK, which claims benefit of the priority of U.S. Provisional Patent Application No. 61/591,980 filed Jan. 29, 2012 entitled MICROFRACTURE PICK. This application further is a continuation of International Application No. PCT/US2014/022537 filed Mar. 10, 2014 entitled MICROFRACTURE PICK, which claims benefit of the priority of U.S. Provisional Patent Application No. 61/781,215 filed Mar. 14, 2013 entitled MICROFRACTURE PICK.

TECHNICAL FIELD

The subject application relates generally to microfracture stimulation, and more specifically to surgical devices for use in performing microfracture stimulation.

BACKGROUND

In the human body, articulating joints are surfaced with hyaline cartilage, which is a durable natural material with a low coefficient-of-friction. Such hyaline cartilage surfaces can become damaged over time when subjected to high levels of repeated loading or injury, such as the loading that can occur when a person runs. This is particularly the case for articulating joints in the lower body that are subject to compressive forces, such as the joints located in the ankle, knee, hip, and spine.

In recent years, the resurfacing of cartilage surfaces has been widely studied in the orthopedic industry. One known method of resurfacing cartilage surfaces is referred to as "microfracture stimulation". Instead of replacing damaged hyaline cartilage with an artificial cartilage implant, microfracture stimulation can be performed to stimulate the human body to replace the damaged cartilage with fibrous cartilage tissue (also referred to herein as "fibrocartilage"). Fibrocartilage is generally not as robust as hyaline cartilage, and typically has a higher coefficient-of-friction compared with that of hyaline cartilage. Nonetheless, such fibrocartilage provides many people with reduced pain, enabling them to assume more active lifestyles.

A conventional microfracture pick for use in performing microfracture stimulation has a handle, a shaft coupled to the handle, and a sharp, optionally angled tip disposed at a distal end of the shaft. For example, conventional microfracture picks can have tips that are optionally bent at angles of about 20°, 40°, 60°, or 90° relative to the longitudinal axis of the shaft. In a typical mode of operation, microfracture stimulation first involves the removal of the damaged layer of cartilage. The thickness of the damaged cartilage layer can typically vary from about 1 mm to 6 mm. The sharp tip of the microfracture pick is then driven about 2 mm to 5 mm through underlying subchondral bone in the region of the removed layer of cartilage to reach a blood supply. The microfracture pick is then removed, causing a small channel to remain in the subchondral bone. The microfracture pick is typically used to create a series of such channels through the subchondral bone. As a result, blood eventually travels along the series of channels and clots in the region of the removed cartilage layer, ultimately causing the formation of fibrocartilage.

When a surgeon uses such a conventional microfracture pick to perforate the subchondral bone of a patient, he or she may experience difficulties manually advancing the sharp tip through a hard cortical layer of the bone. This can be problematic since not advancing the microfracture pick deep enough into the bone may prohibit the formation of fibrocartilage in the region of the removed cartilage layer. To aid in advancing the sharp tip of the microfracture pick through the subchondral bone, surgeons have traditionally used a hammer or mallet to strike an end of the handle of the microfracture pick, while applying a downward pressure to the handle. However, such use of a hammer or mallet has drawbacks in that it can produce a shear force at the tip of the microfracture pick, potentially causing the tip to become broken or otherwise damaged. Such a broken tip can become a loose body in the surgical site, and can cause a delay in the progress of the microfracture procedure. In addition, the tip can skive across the bone surface, potentially causing the microfracture pick to impinge on and possibly damage surrounding tissue surfaces.

To address this problem, a strike plate can be directly attached to the shaft or handle of the conventional microfracture pick. Such a strike plate is typically attached to the shaft or handle perpendicular to the direction of the sharp tip of the microfracture pick. When a surgeon strikes the strike plate with a hammer or mallet, the resulting force causes the tip of the microfracture pick to advance through the subchondral bone. Directly attaching a strike plate to the shaft or handle of a microfracture pick also has drawbacks, however, in that it can make the microfracture pick heavy and cumbersome. The act of striking the strike plate so close to the patient's body can also be problematic, especially when performed near delicate joint access locations such as the ankle. The strike plate can also interfere with the microfracture procedure by preventing complete access to the surgical site, potentially making it extremely difficult for the surgeon to treat the entire affected surface area of the bone.

It would therefore be desirable to have a microfracture pick that avoids at least some of the drawbacks of the conventional microfracture picks discussed above.

SUMMARY

In accordance with the subject application, a surgical device (referred to herein as a "microfracture pick") is disclosed that has features configured to aid a user in advancing the microfracture pick through bone. In one aspect, the disclosed microfracture pick includes at least one elongated member such as a shaft having a proximal end and a distal end, a sharp, optionally angled tip disposed at the distal end of the shaft, an optional handle coupled to the proximal end of the shaft, and at least one engaging feature disposed at one or more locations on the shaft or handle for engaging a complementary feature of a strike instrument. In an exemplary aspect, the strike instrument includes at least one elongated member such as a shaft having a proximal end and a distal end, the complementary feature disposed at the distal end of the shaft, an optional handle having a proximal end as well as a distal end coupled to the proximal end of the shaft, and an impact surface disposed at the proximal end of the shaft or handle. In a further exemplary aspect, the engaging feature disposed on the shaft or handle of the microfracture pick is configured as a receptacle, and the complementary feature of the strike instrument is configured to operatively engage the receptacle on the microfracture pick. In another exemplary aspect, the complementary feature of the strike instrument is configured as a receptacle, and the engaging feature disposed on the shaft or handle of the microfracture pick is configured to operatively engage the receptacle on the strike instrument.

In another aspect, a system for use in performing a microfracture procedure is disclosed that includes a strike instrument having an elongated member such as a handle with a proximal end, a distal end, and a hole located near the distal end of the handle, a strike pin configured to pass through the hole in the handle, an impact surface located at one end of the strike pin, and a complementary feature located at the other end of the strike pin. The system further includes a surgical device having an optional handle, an elongated member such as a shaft with a distal end, an engaging feature located on the shaft or handle, and a sharp, optionally angled tip located at the distal end of the shaft. The engaging feature of the surgical device is operative to engage the complementary feature of the strike instrument. Moreover, the handle of the strike instrument is configured to be disposed generally parallel to the longitudinal axis of the surgical device to facilitate engagement of the engaging feature with the complementary feature. Upon striking the impact surface of the strike instrument, a force is produced that is translated via the shaft of the surgical device through the tip.

In a further aspect, a method of performing a microfracture procedure is disclosed that includes providing a surgical device having at least one elongated member such as a shaft with a proximal end and a distal end, a sharp, optionally angled tip disposed at the distal end of the shaft, an optional handle coupled to the proximal end of the shaft, and at least one engaging feature disposed at one or more locations on the shaft or handle for engaging a complementary feature of a strike instrument. The method also includes locating the tip at a desired point of stimulation, and striking an impact surface of the strike instrument to produce a force that is translated via the shaft through the tip. The tip is then removed from the desired point of stimulation. Such use of a strike instrument in performing a microfracture procedure allows a surgeon to place the microfracture perforation at the desired point of stimulation with increased accuracy. Such use of the strike instrument also reduces the amount of force that the surgeon must manually apply to the microfracture pick to achieve the desired microfracture perforation.

By providing a microfracture pick having an elongated member with a proximal end, a distal end, a sharp, optionally angled tip disposed at the distal end of the elongated member, and at least one engaging feature disposed at one or more locations on the elongated member for engaging a complementary feature of a strike instrument, a user can use the strike instrument to produce a force that is translated via the elongated member of the microfracture pick through the tip, thereby making penetration of the tip through bone more effective. As a result, the number of instances of fracturing the tip during use can be reduced. Further, the number of instances of skiving the tip along the bone surface during use can be substantially eliminated.

Other features, functions, and aspects of the invention will be evident from the Detailed Description that follows.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings:

FIGS. 10-18 are further views illustrating various alternative embodiments of the microfracture pick and the strike instrument of FIG. 1.

DETAILED DESCRIPTION

The disclosures of International Application No. PCT/US2014/022537 filed Mar. 10, 2014 entitled MICROFRACTURE PICK, U.S. Provisional Patent Application No. 61/781,215 filed Mar. 14, 2013 entitled MICROFRACTURE PICK, International Application No. PCT/US2013/021400 filed Jan. 14, 2013 entitled MICROFRACTURE PICK, and U.S. Provisional Patent Application No. 61/591,980 filed Jan. 29, 2012 entitled MICROFRACTURE PICK, are hereby incorporated herein by reference in their entirety.

A microfracture pick is disclosed having features configured to aid a user in advancing the microfracture pick through bone. The microfracture pick has a shaft with a proximal end, a distal end, a sharp, optionally angled tip located at the distal end of the shaft, and at least one engaging feature disposed at one or more locations on the shaft for engaging a complementary feature of a strike instrument. By striking an impact surface of the strike instrument, the user can produce a force that is translated via the shaft of the microfracture pick through its tip, thereby making penetration of the tip through the bone more effective.

Figure 1:
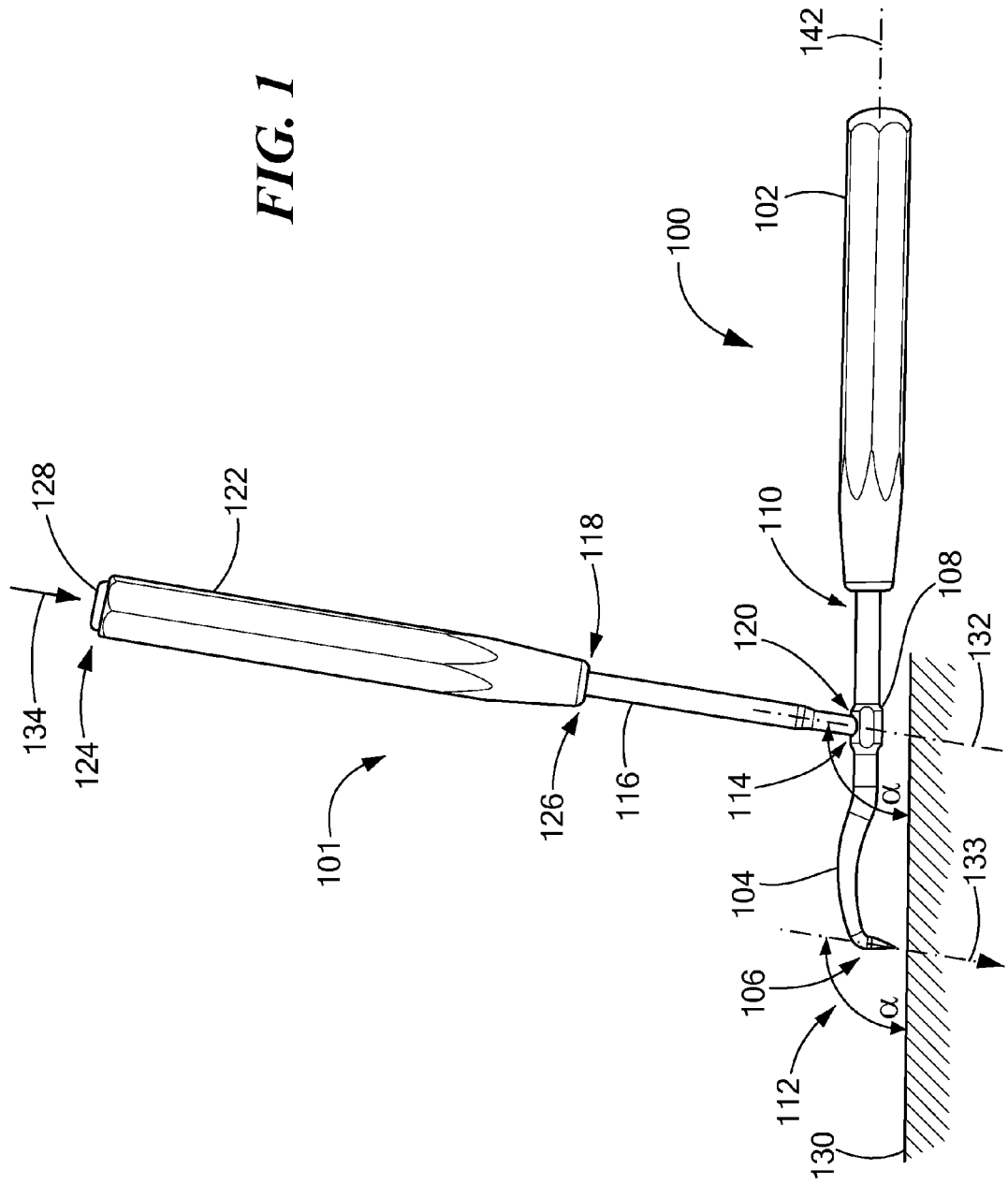
FIG. 1 is a side view illustrating an exemplary microfracture pick, and an exemplary strike instrument configured to operatively engage the microfracture pick, in accordance with the subject application.

FIG. 1 depicts an illustrative embodiment of a microfracture pick 100, in accordance with the subject application. As shown in FIG. 1, the microfracture pick 100 has a proximal portion that includes an elongated handle 102, and a distal portion that includes a generally elongated shaft 104, which has a proximal end 110 and a distal end 112. The handle 102 is coupled to the proximal end 110 of the shaft 104. The microfracture pick 100 further includes a sharp, optionally angled tip 106 located at the distal end 112 of the shaft 104, and an engaging feature 108 disposed at a fixed location on the shaft 104 for engaging a complementary feature 114 of a strike instrument 101. The strike instrument 101 can include a shaft 116 that has a proximal end 118 and a distal end 120, and the complementary feature 114 can be located at the distal end 120 of the shaft 116. The strike instrument 101 can further include a handle 122 having a proximal end 124 and a distal end 126 coupled to the proximal end 118 of the shaft 116, and an impact surface 128 located at the proximal end 124 of the handle 122.

It is noted that the handle 122, the shaft 116, and the impact surface 128 of the strike instrument 101 can be implemented as a single component. Likewise, the handle 102 and the shaft 104 of the microfracture pick 100 can be implemented as a single component. It is also noted that the shaft 104 of the microfracture pick 100, as well as the shaft 116 of the strike instrument 101, can be made from machined medical grade material such as hardened stainless steel, or any other suitable material. Further, the handle 102 of the microfracture pick 100, as well as the handle 122 of the strike instrument 101, can have a cylindrical shape, or any other suitable shape. In some embodiments, the handle 102 of the microfracture pick 100 may be omitted. Moreover, the tip 106 can be optionally bent at an angle of about 20°, 40°, 60°, 90°, or any other suitable angle, relative to the longitudinal axis 142 of the microfracture pick 100. For example, the tip 106 can be optionally bent at an angle greater than 90° relative to the longitudinal axis 142 by bending the tip 106 back toward the handle 102.

During use, the direction 133 of the sharp tip 106 of the microfracture pick 100 can be aligned at an angle α relative to a surface 130 (see FIG. 1), which can correspond to the surface of bone. Once the complementary feature 114 of the strike instrument 101 is engaged with the engaging feature 108 of the microfracture pick 100, the longitudinal axis 132 the strike instrument 101 can be aligned at about the same angle α relative to the surface 130. Accordingly, when a user (e.g., a surgeon) strikes the impact surface 128 of the strike instrument 101 with a hammer, mallet, or any other suitable striking implement, a force 134 is produced that is translated via the shaft 104 of the microfracture pick 100 through the tip 106.

Figure 2:
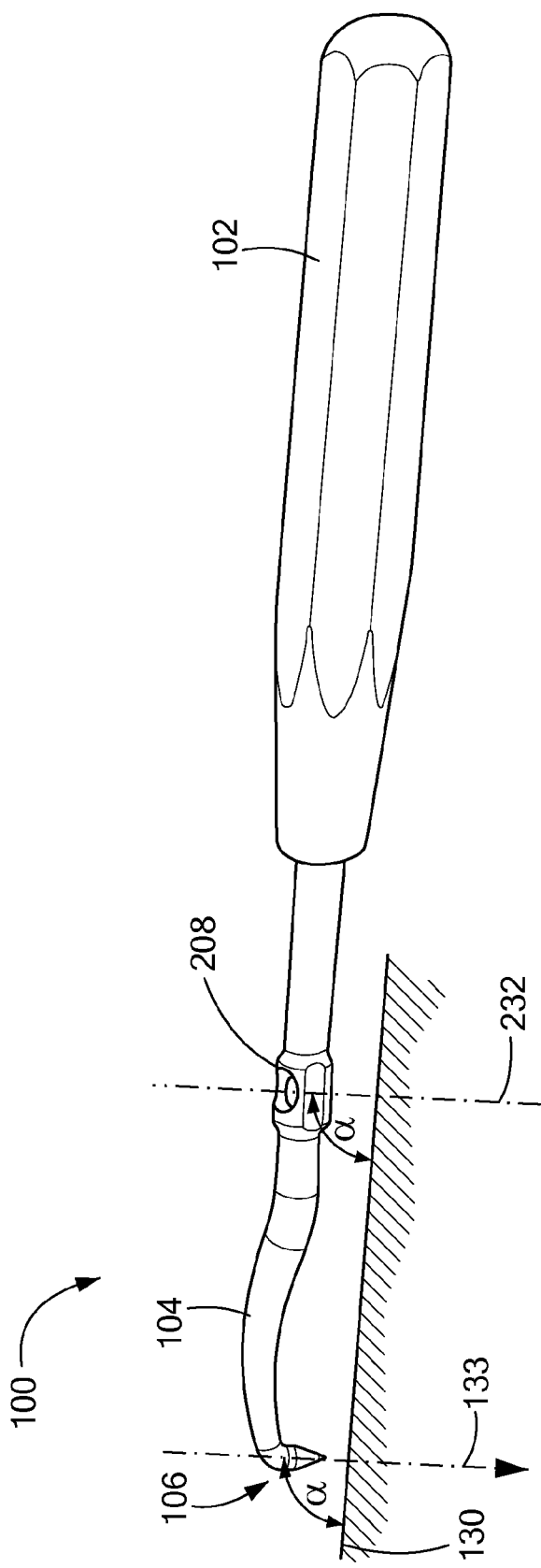
FIG. 2 is a perspective view illustrating the microfracture pick of FIG. 1.

FIG. 2 depicts a perspective view of the microfracture pick 100, including the handle 102, the shaft 104, the sharp, optionally angled tip 106, and the engaging feature (see reference numeral 108; FIG. 1), which is configured as a receptacle 208. In this illustrative embodiment, the complementary feature 114 of the strike instrument 101 (see FIG. 1) is configured to operatively engage the receptacle 208 of the microfracture pick 100. Accordingly, if the surgeon experiences difficulties advancing the tip 106 of microfracture pick 100 through bone, he or she can insert the complementary feature 114 of the strike instrument 101 into the receptacle 208 of the microfracture pick 100, and strike the impact surface 128 of the strike instrument 101 one or more times with a hammer or mallet to produce a force, thereby facilitating advancement of the tip 106 through the bone.

Figure 3:
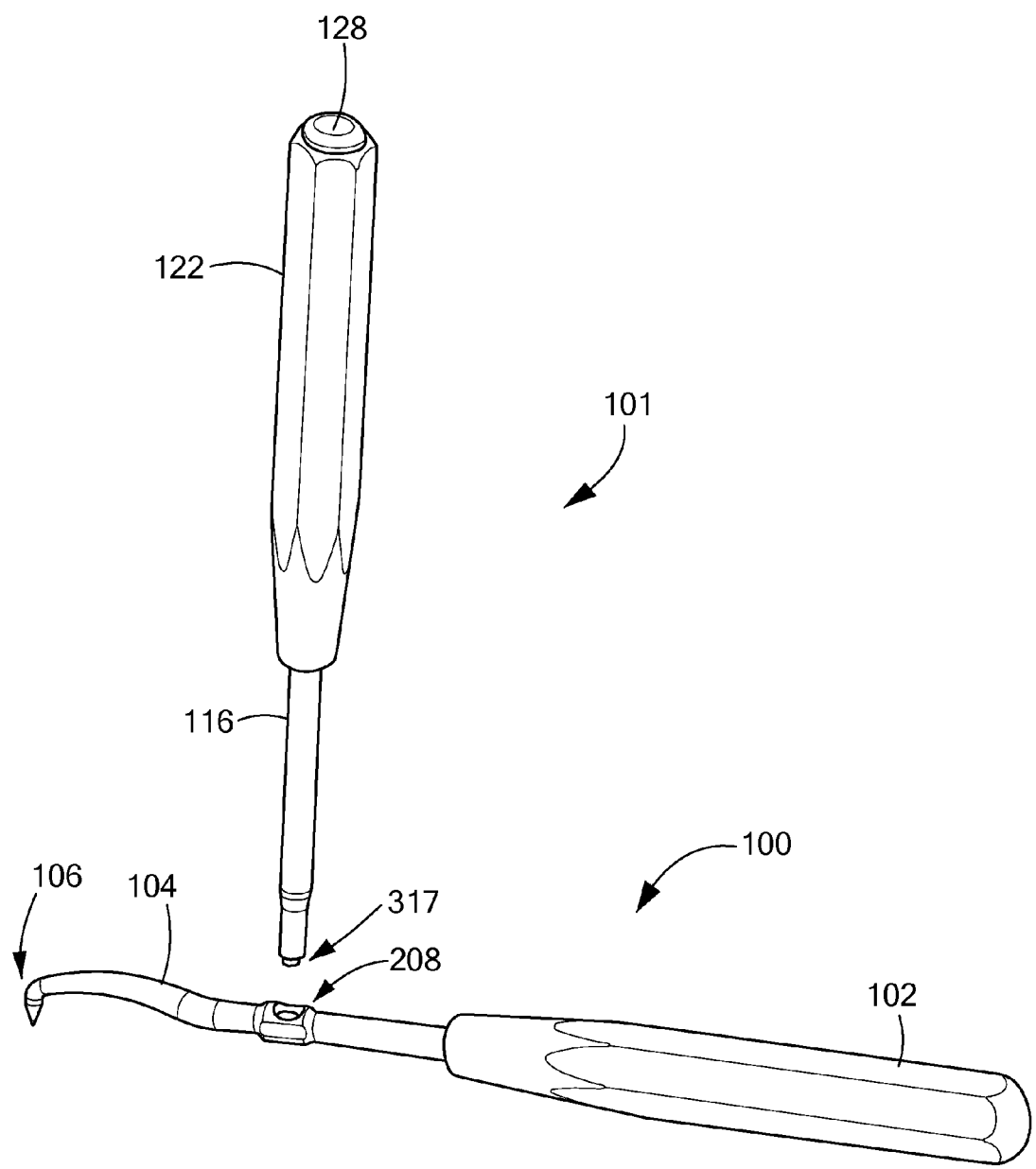
FIG. 3 is a perspective view illustrating the microfracture pick of FIG. 1, and the strike instrument of FIG. 1.

FIG. 3 depicts a perspective view illustrating the microfracture pick 100 and the strike instrument 101, in which the complementary feature (see reference numeral 114; FIG. 1) is configured to include an optional nub 317 that can be temporarily or permanently fixated to the receptacle 208 of the microfracture pick 100. For example, the optional nub 317, or an end of the shaft 116 without the nub 317, can be temporarily or permanently fixated to the receptacle 208 by way of threading, a press fit, a lever lock, a cam lock, a snap fit, a set screw, a taper fit, a luer lock (with or without taper), or any other suitable mechanism.

Figure 4:
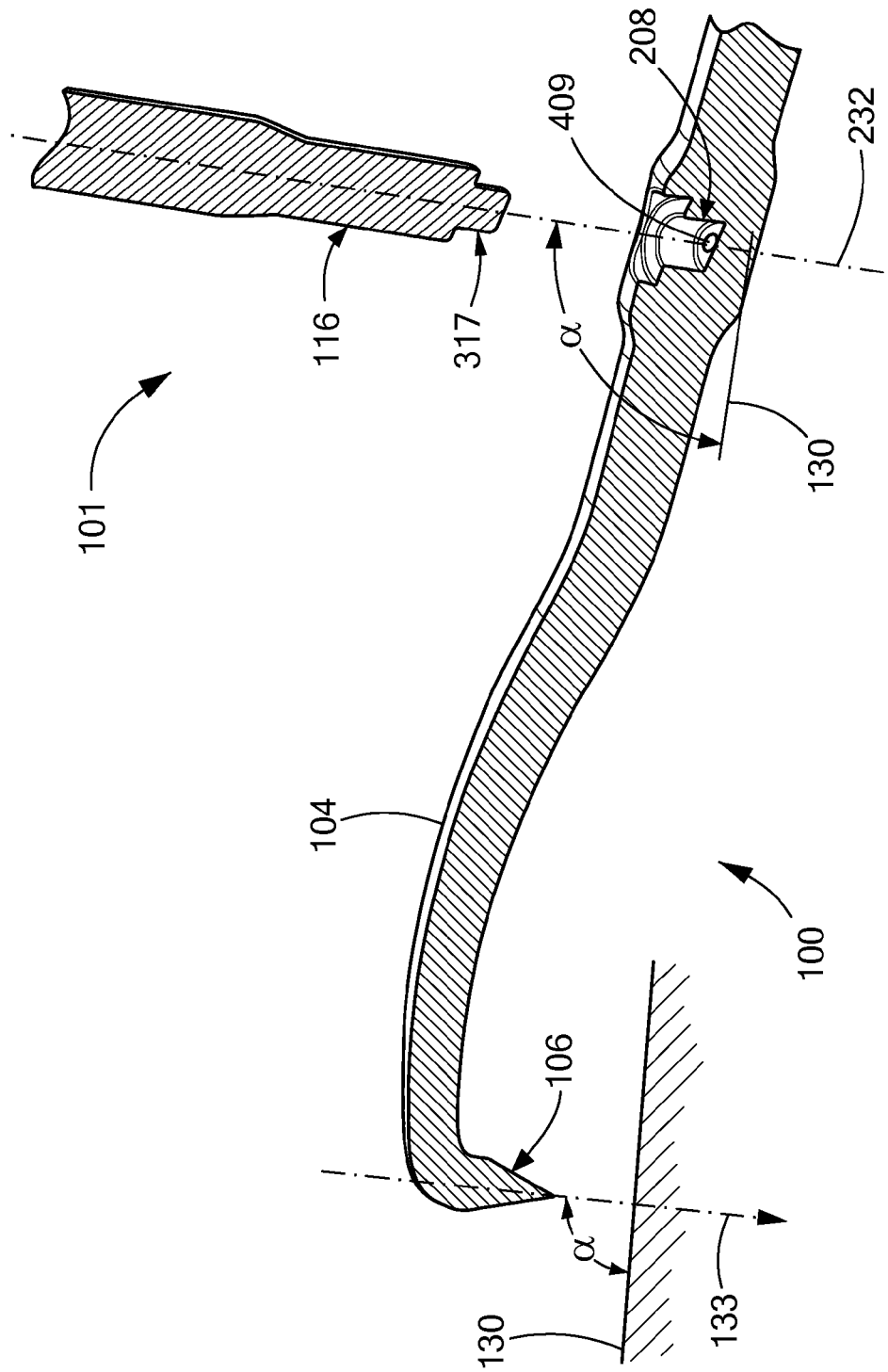
FIG. 4 is a sectional view illustrating the microfracture pick of FIG. 1, and the strike instrument of FIG. 1, including an engaging feature of the microfracture pick, and a complementary feature of the strike instrument.

FIG. 4 depicts a sectional view illustrating the microfracture pick 100 including the receptacle 208, as well as the strike instrument 101 including the optional nub 317. In the sectional view of FIG. 4, the receptacle 208 is illustrated as being substantially internal to the shaft 104 of the microfracture pick 100. For example, the nub 317 can be configured as a male connector or any other suitable connector, and the receptacle 208 can be configured as a female connector or any other suitable connector. In some embodiments, the microfracture pick 100 can be configured to include a male connector, and the strike instrument 101 can be configured to include a female connector for engaging the male connector of the microfracture pick 100. Such male and female connectors can be temporarily or permanently fixated to one another by way of threading, a press fit, a lever lock, a cam lock, a snap fit, a set screw, a taper fit, a luer lock (with or without taper), or any other suitable mechanism. Further, the receptacle 208 can be configured to include an external drain hole 409 for sterilization and/or dry time purposes, as well as for avoiding a possible build-up of fluid in the receptacle 208 during use. For example, the external drain hole 409 can have a diameter of about 2 mm, or any other suitable diameter.

Figure 5:
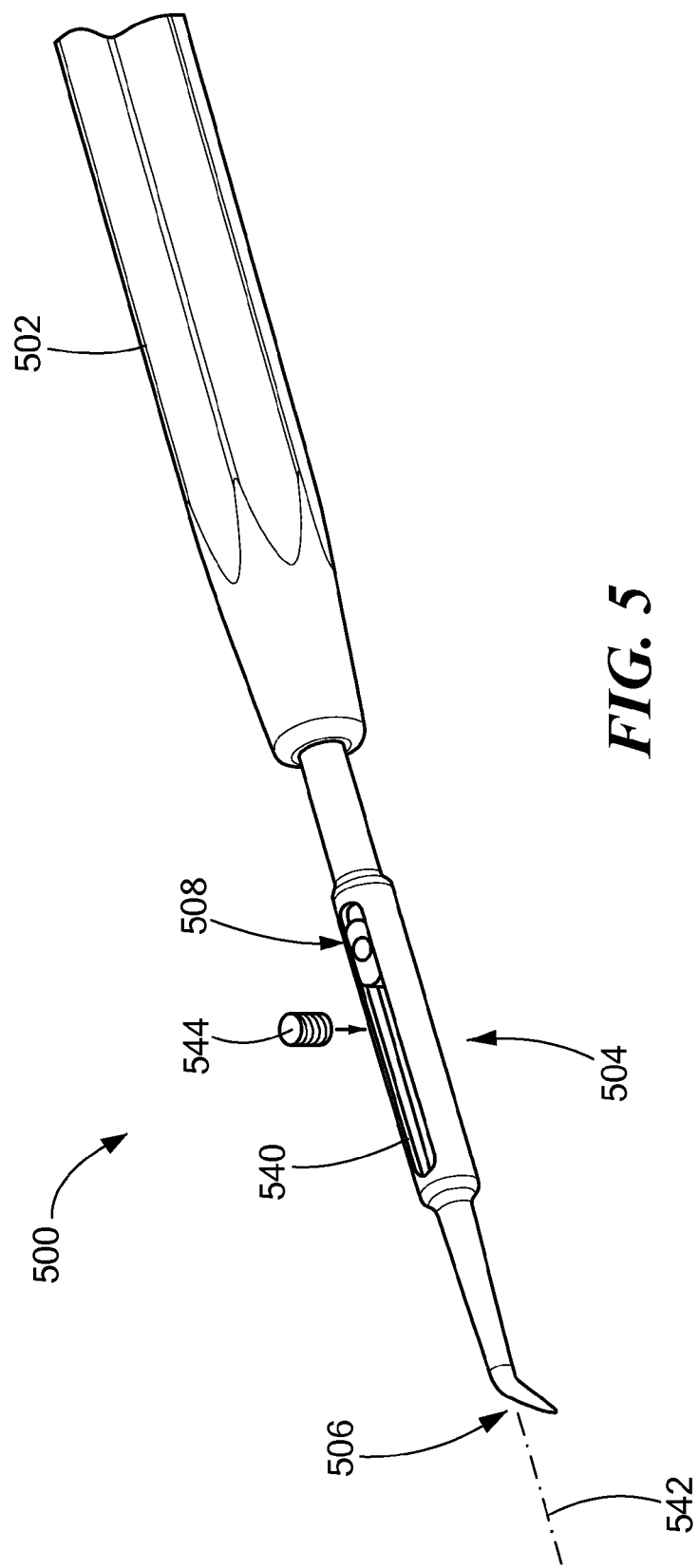
FIG. 5 is a perspective view illustrating a first alternative embodiment of the microfracture pick of FIG. 1.

Having described the above illustrative embodiments of the disclosed microfracture pick, other alternative embodiments or variations may be made. For example, it was described with reference to FIG. 1 that the microfracture pick 100 includes the engaging feature 108 disposed at a fixed location on the shaft 104 for engaging the complementary feature 114 of the strike instrument 101. FIG. 5 depicts an alternative embodiment of a microfracture pick 500 that includes a handle 502, a shaft 504, a sharp, optionally angled tip 506, and an engaging feature 508. As shown in FIG. 5, the shaft 504 is configured to incorporate a channel 540 along at least a portion of its length, and the engaging feature 508 is configured to engage and slide along the channel 540 to a desired location on the shaft 504. The channel 540 is substantially parallel to the longitudinal axis 542 of the shaft 504. Further, the engaging feature 508 can be configured to include a receptacle like the receptacle 208 of FIG. 2. Once the engaging feature 508 is slid or otherwise moved along the channel 540 to the desired location on the shaft 504, the engaging feature 508 can be temporarily or permanently fixated at that location on the shaft 504 by at least one stop member 544, which, as shown in FIG. 5, can be inserted into or otherwise engaged with the channel 540 adjacent the engaging feature 508, or by any other suitable mechanism. In alternative embodiments, the engaging feature 508 can be temporarily or permanently fixated at a desired location on the shaft 504. In further alternative embodiments, the engaging feature 508 can be removed if it is not required to perform the microfracture procedure.

Figure 6:
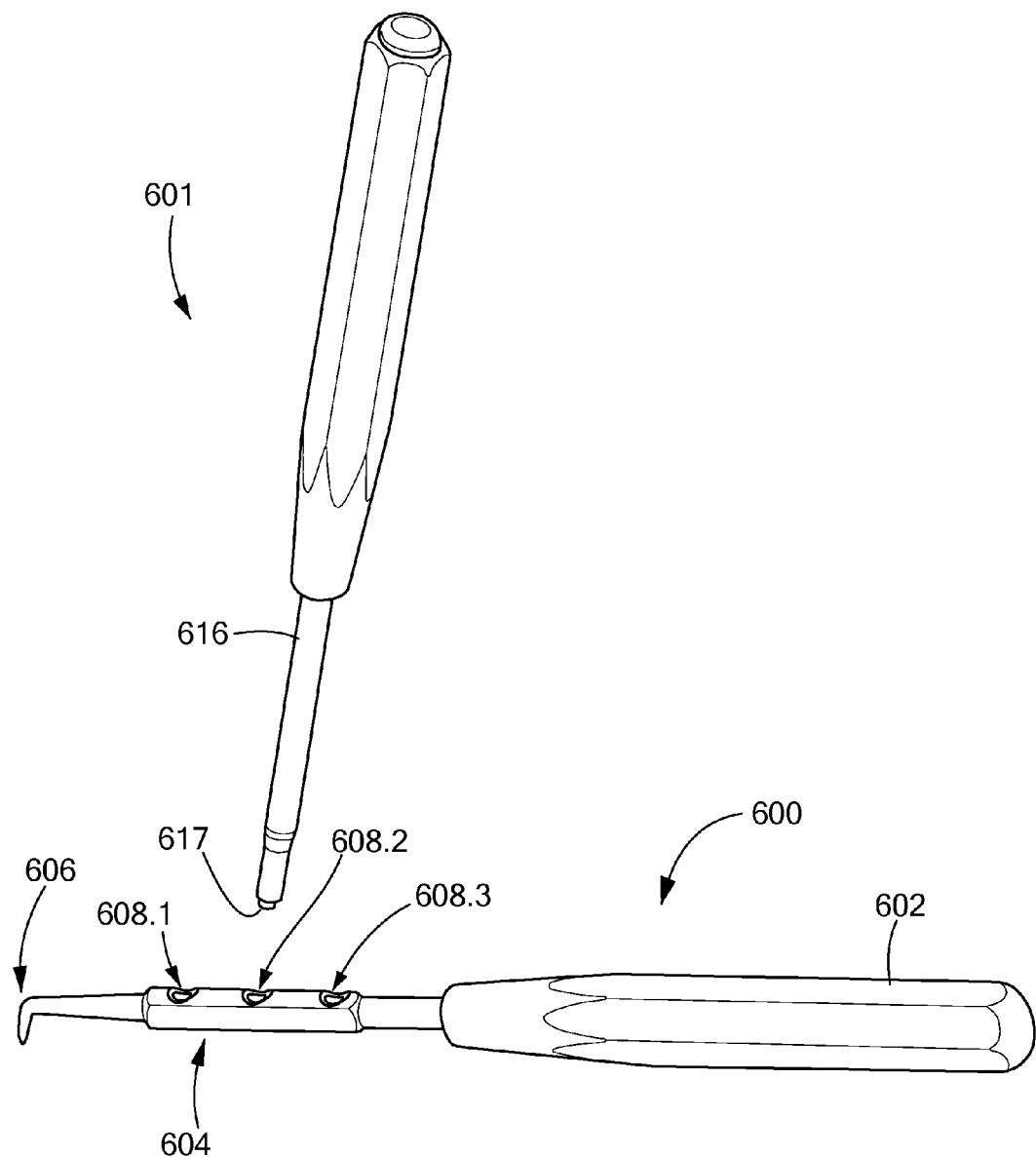
FIG. 6 is a perspective view illustrating a second alternative embodiment of the microfracture pick of FIG. 1.

FIG. 6 depicts another alternative embodiment of a microfracture pick 600 that includes a handle 602, a shaft 604, a sharp, optionally angled tip 606, and a plurality of engaging features 608.1, 608.2, 608.3 disposed at a plurality of fixed locations, respectively, on the shaft 604. FIG. 6 depicts three (3) such engaging features on the shaft 604 for purposes of illustration. It should be understood, however, that the microfracture pick 600 can include any suitable number of engaging features disposed at respective locations on the shaft 604. For example, each of the plurality of engaging features 608.1, 608.2, 608.3 can be configured to include a receptacle like the receptacle 208 of FIG. 2. FIG. 6 further depicts a strike instrument 601, in which the complementary feature is configured to include an optional nub 617 at an end of a shaft 616 that can be temporarily or permanently fixated to a selected one of the plurality of engaging features 608.1, 608.2, 608.3 on the shaft 604. For example, the optional nub 617, or the end of the shaft 616 without the nub 617, can be temporarily or permanently fixated to the selected engaging feature 608.1, 608.2, or 608.3 by way of threading, a press fit, a lever lock, a cam lock, a snap fit, a set screw, a taper fit, a luer lock (with or without taper), or any other suitable mechanism.

Figure 7:
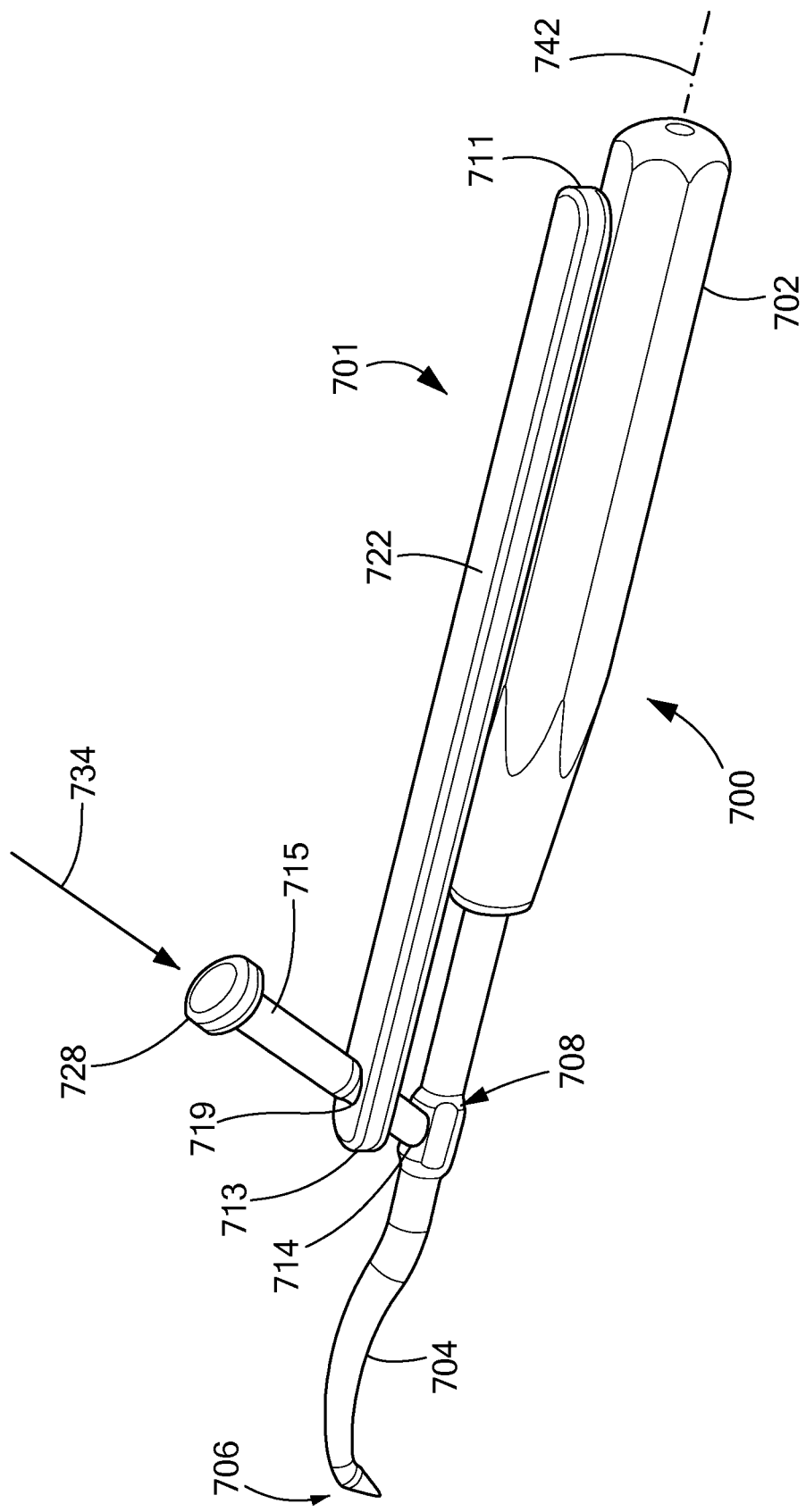
FIG. 7 is a perspective view illustrating an exemplary microfracture pick, and an alternative embodiment of the strike instrument of FIG. 1.

FIG. 7 depicts an alternative embodiment of a strike instrument 701, which includes a complementary feature 714 for engaging an engaging feature 708 of a microfracture pick 700. As shown in FIG. 7, the strike instrument 701 includes a handle 722 having a proximal end 711, a distal end 713, and a hole 719 located near the distal end 713 of the handle 722. The strike instrument 701 further includes a strike pin 715 configured to pass snugly through the hole 719, the complementary feature 714 located at one end of the strike pin 715, and an impact surface 728 located at the other end of the strike pin 715. It is noted that the handle 722, the strike pin 715, and the impact surface 728 of the strike instrument 701 can be implemented as a single component. As further shown in FIG. 7, the microfracture pick 700 includes a handle 702, a shaft 704, the engaging feature 708 located on the shaft 704, and a sharp, optionally angled tip 706 located at a distal end of the shaft 704. It is noted that the strike pin 715 can be temporarily or permanently fixated in the hole 719 through the handle 722 of the strike instrument 701.

Figure 8:
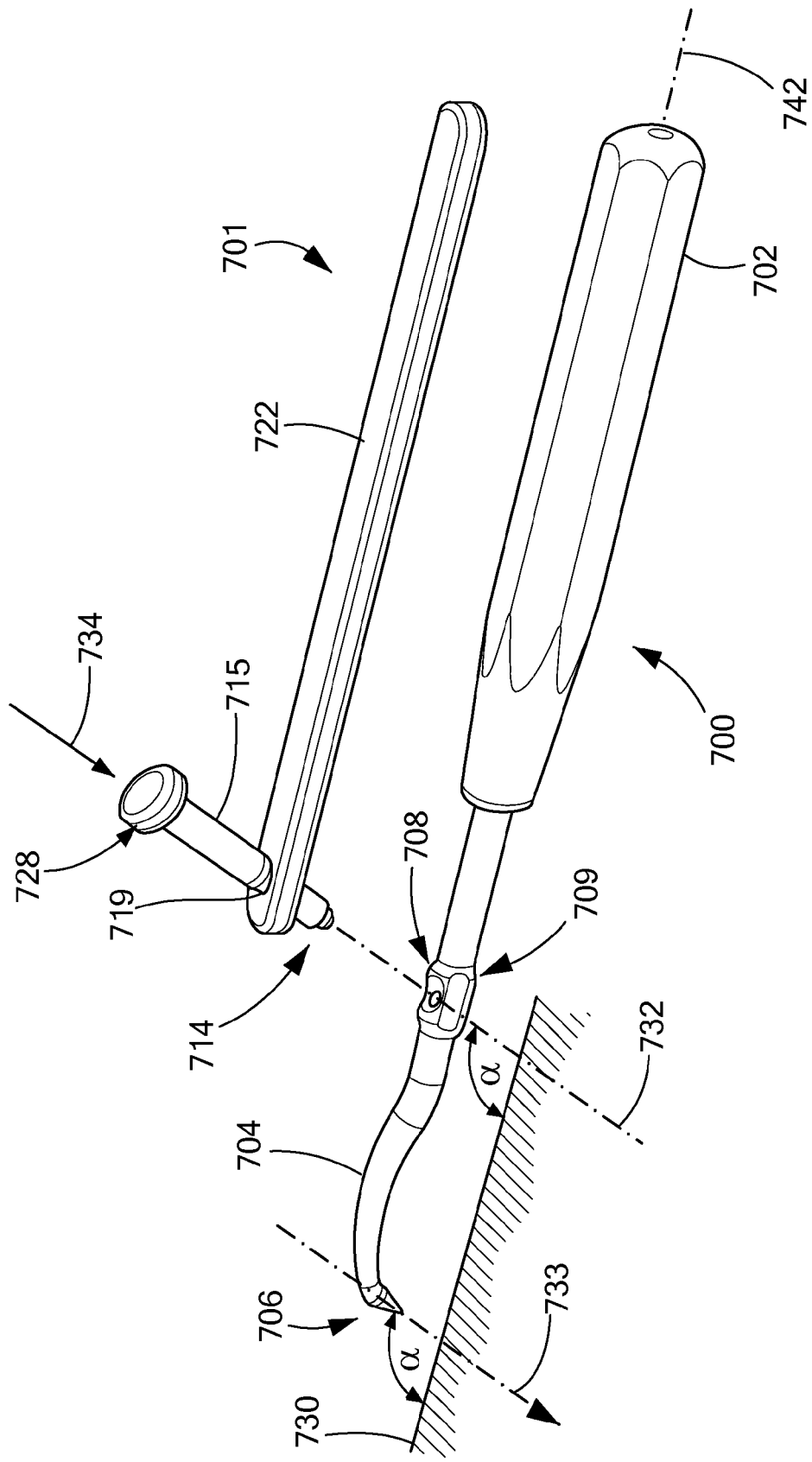
FIG. 8 is another perspective view illustrating the microfracture pick of FIG. 7, and the strike instrument of FIG. 7.

FIG. 8 depicts the microfracture pick 700 and the strike instrument 701, in which the complementary feature 714 of the strike instrument 701 is configured to include an optional nub 717, and the engaging feature 708 of the microfracture pick 700 is configured to include a receptacle 709. For example, the optional nub 717, or an end of the strike pin 715 without the nub 717, can be temporarily or permanently fixated to the receptacle 709 of the microfracture pick 700 by way of threading, a press fit, a lever lock, a cam lock, a snap fit, a set screw, a taper fit, a luer lock (with or without taper), or any other suitable mechanism.

During use, the handle 722 of the strike instrument 701 can be temporarily or permanently fixated to the handle 702 of the microfracture pick 700 substantially parallel to its longitudinal axis 742, thereby allowing the surgeon to hold both the handle 722 of the strike instrument 701 and the handle 702 of the microfracture pick 700 with the same hand. For example, the handle 722 of the strike instrument 701 can be temporarily or permanently fixated to the handle 702 of the microfracture pick 700 by way of threading, a press fit, a lever lock, a cam lock, a snap fit, a set screw, a taper fit, a luer lock (with or without taper), a bayonet mount, or any other suitable mechanism. Further, the strike pin 715 can pass through the hole 719 in the handle 722 to engage the nub 717 of the strike instrument 701 with the receptacle 709 of the microfracture pick 700. Accordingly, if the surgeon experiences difficulties advancing the tip 706 of microfracture pick 700 through bone, he or she can strike the impact surface 728 of the strike pin 715 one or more times with a hammer or mallet to produce a force 734, thereby facilitating advancement of the tip 706 through the bone.

It was further described herein that the microfracture pick could include a receptacle on its shaft, and the strike instrument could include an optional nub on its shaft for engaging the receptacle. In further alternative embodiments, the microfracture pick can include at least one engaging feature configured like a nub at a fixed or movable location on its shaft, and the strike instrument can include at least one complementary feature configured like a receptacle on its shaft. For example, such a receptacle on the shaft of the strike instrument can have a forked configuration for cradling the nub on the shaft of the microfracture pick. Moreover, the microfracture pick can alternatively include a nub or receptacle, such as a male or female connector, on its handle for engaging a complementary feature on the strike instrument. Likewise, the strike instrument can alternatively include a nub or receptacle, such as a male or female connector, on its handle for complementarily engaging an engaging feature on the microfracture pick.

It was also described herein that the microfracture pick could include a plurality of engaging features disposed at respective locations on its shaft for engaging a complementary feature of the strike instrument. In further alternative embodiments, the plurality of engaging features of the microfracture pick can be configured as respective receptacles having parallel or non-parallel axes. In addition, the plurality of engaging features of the microfracture pick can each be configured to accept a different configuration of the complementary feature of the strike instrument.

Figure 9:
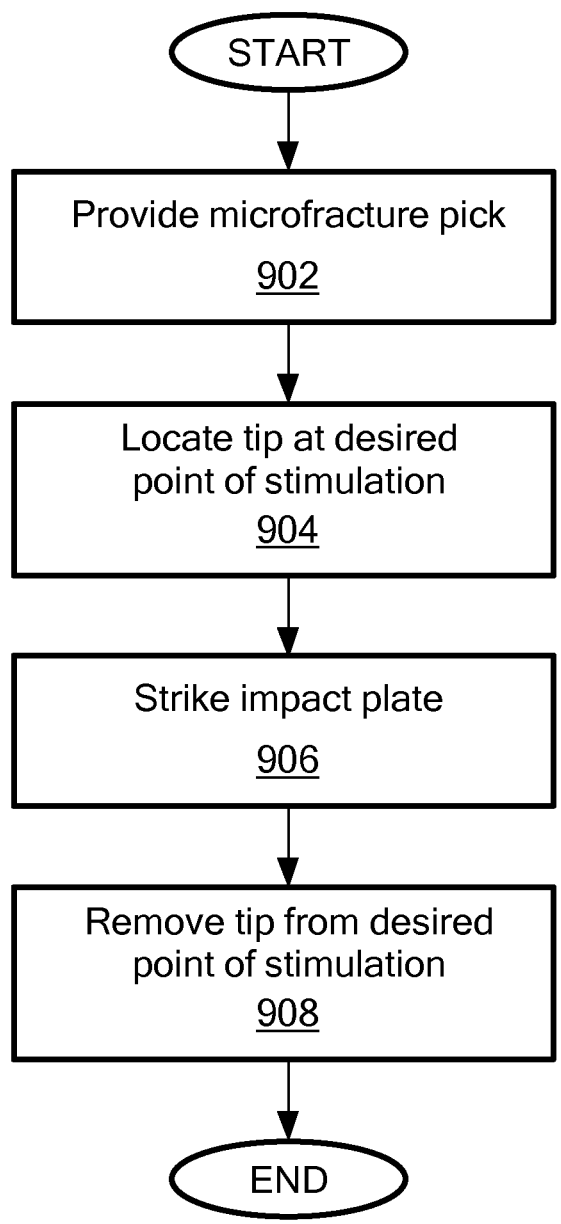
FIG. 9 is a flow diagram illustrating a method of performing a microfracture procedure using the microfracture pick of FIG. 1.

A method of performing a microfracture procedure, using the disclosed microfracture pick, is described below with reference to FIG. 9. As depicted in block 902, the method includes providing a microfracture pick having a shaft with a proximal end and a distal end, an optionally angled tip disposed at the distal end of the shaft, a handle coupled to the proximal end of the shaft, and at least one engaging feature disposed at one or more locations on the shaft for engaging a complementary feature of a strike instrument. As depicted in block 904, the tip is located at a desired point of stimulation. For example, while locating the tip at the desired point of stimulation, at least a portion of the shaft may be inserted into an arthroscopic cannula. As depicted in block 906, an impact surface of the strike instrument is struck by a hammer or mallet to produce a force that is translated via the shaft through the tip at the desired point of stimulation. As depicted in block 908, the tip is then removed from the desired point of stimulation.

Figure 10:
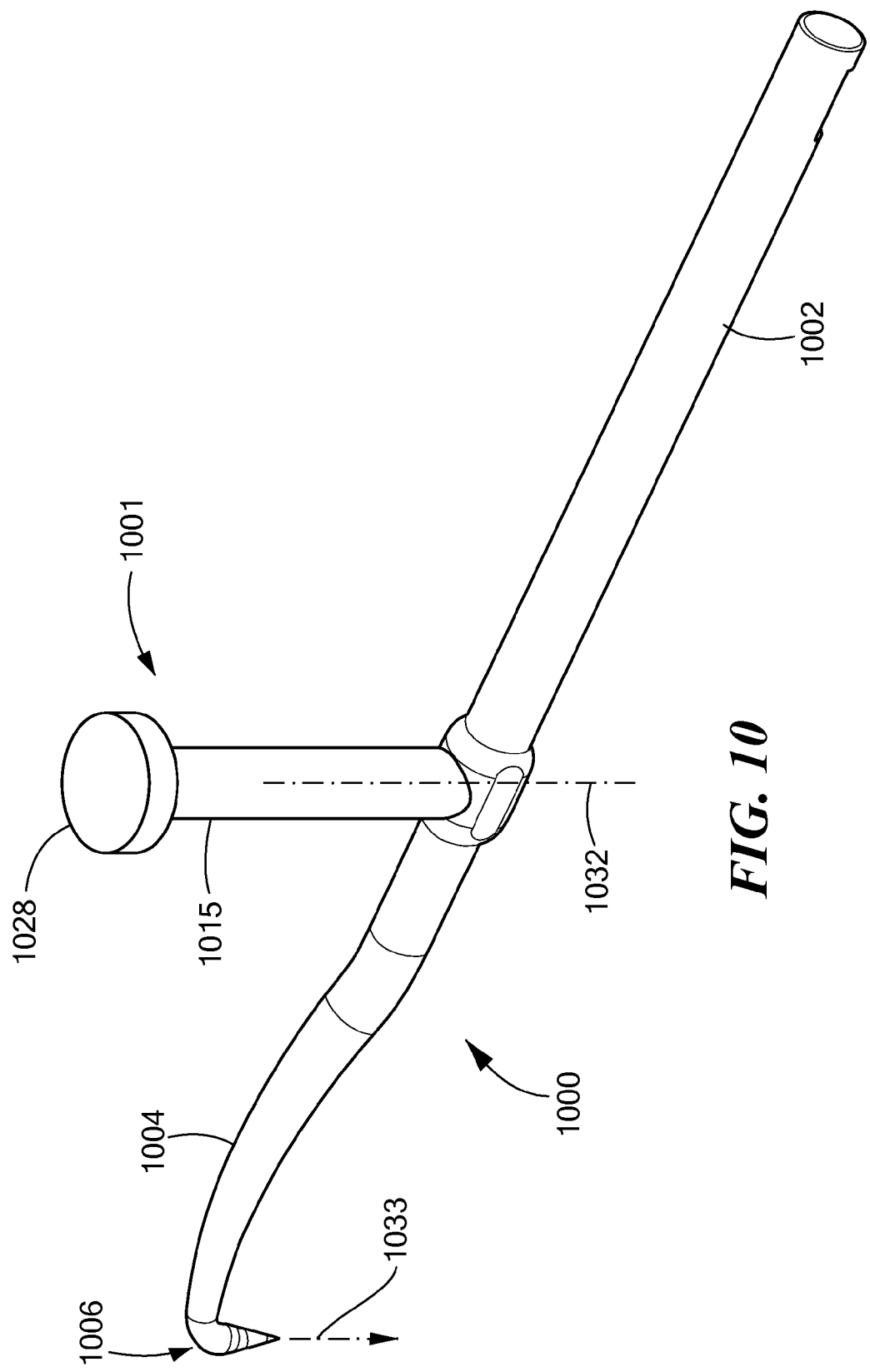

FIGS. 10-18 depict further alternative embodiments of the disclosed microfracture pick and strike instrument. FIG. 10 depicts a microfracture pick 1000 and a strike instrument 1001 that are configured and arranged as a singular component. As shown in FIG. 10, the microfracture pick 1000 includes a handle 1002, a shaft 1004, and an optionally angled tip 1006 located at a distal end of the shaft 1004. The strike instrument 1001 includes a strike pin 1015, and an impact surface 1028 located at one end of the strike pin 1015. Because the microfracture pick 1000 and the strike instrument 1001 are configured and arranged as a singular component, the strike pin 1015 can provide a fixed strike zone for the microfracture pick 1000. It is noted that, in the singular component configuration of FIG. 10, the longitudinal axis 1032 of the strike pin 1015 may be parallel or non-parallel with respect to the direction 1033 of the tip 1006. Further, in one or more alternative embodiments, one or more strike zones for the microfracture pick 1000 may be provided at various locations and/or angles on either the shaft 1004 or the handle 1002 of the microfracture pick 1000.

Figure 11:
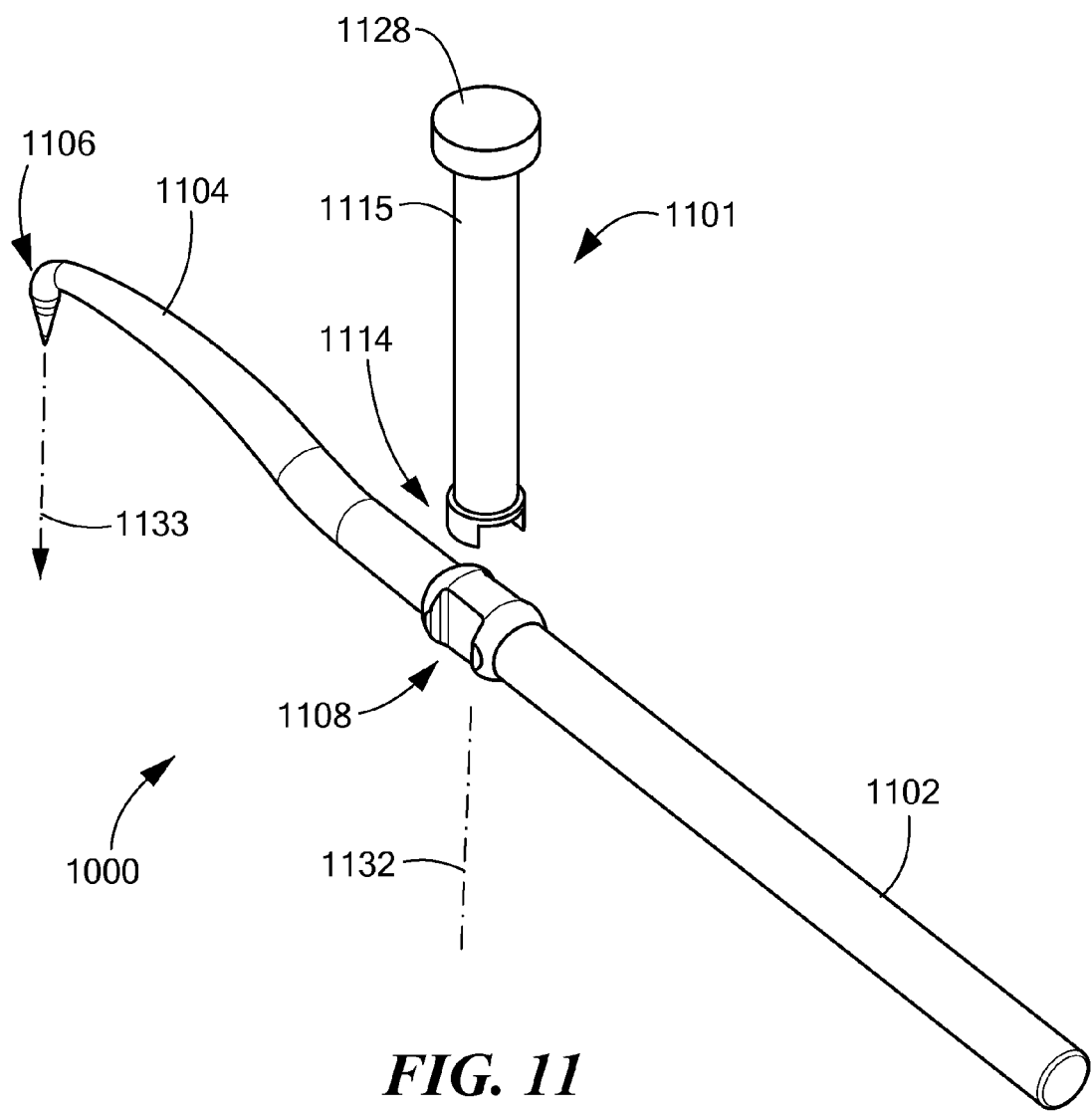

FIG. 11 depicts a strike instrument 1101 that includes a forked complementary feature 1114 for engaging an engaging feature 1108 of a microfracture pick 1100. The microfracture pick 1100 further includes a handle 1102, a shaft 1104, and an optionally angled tip 1106 located at a distal end of the shaft 1104. The strike instrument 1101 further includes a strike pin 1115, and an impact surface 1128 located at one end of the strike pin 1115. For example, the forked feature 1114 of the strike instrument 1101 may have two prongs, as shown, or any other suitable number of prong(s). In one embodiment, the strike instrument 1101 may include a complementary feature for engaging a forked engaging feature of the microfracture pick 1100. It is noted that the longitudinal axis 1132 of the strike pin 1115 may be parallel or non-parallel with respect to the direction 1133 of the tip 1106.

Figure 12:
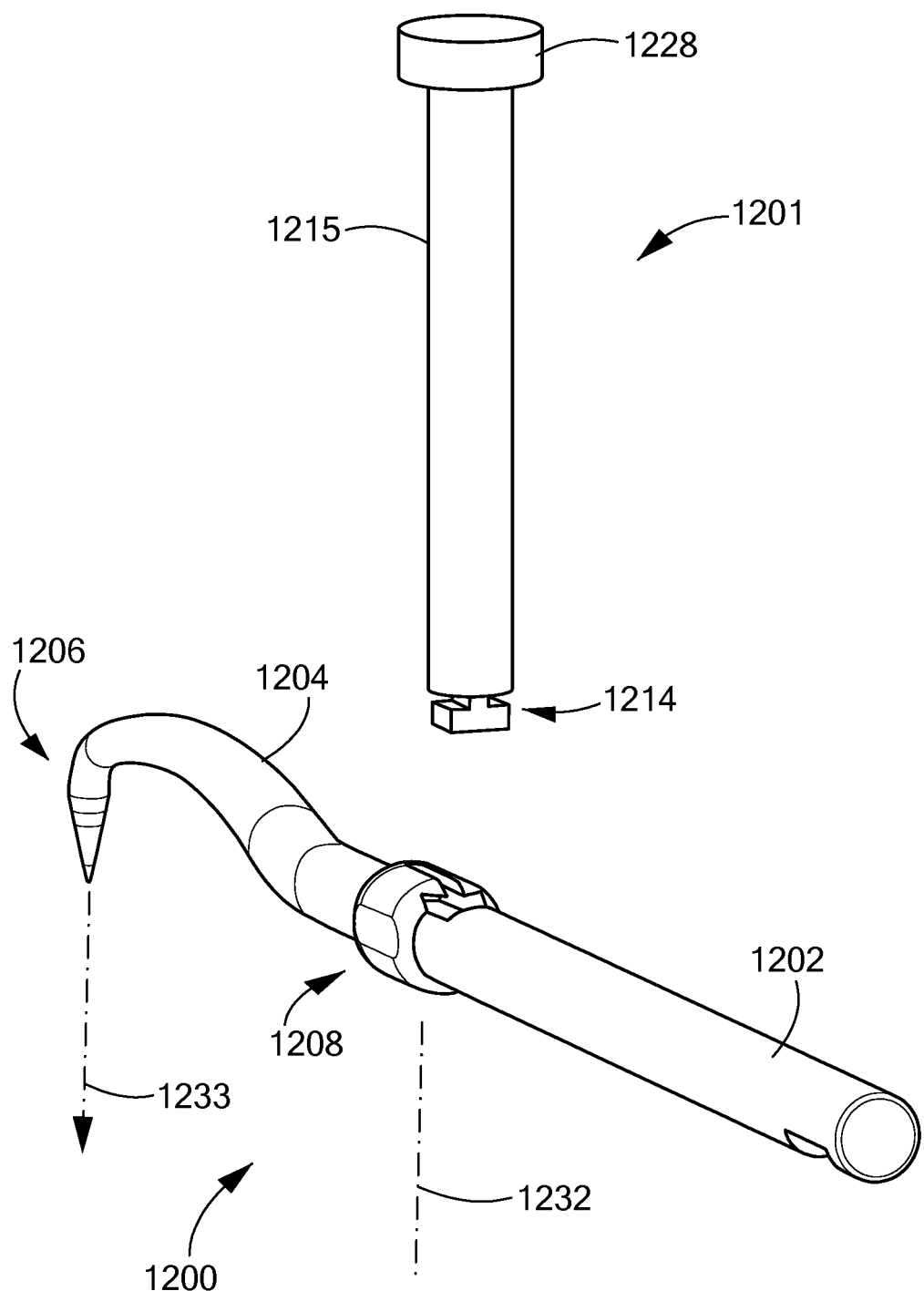

FIG. 12 depicts a strike instrument 1201 that includes a T-shaped (or other similarly shaped) "male" complementary feature 1214 for engaging a slotted "female" engaging feature 1208 of a microfracture pick 1200. The microfracture pick 1200 further includes a handle 1202, a shaft 1204, and an optionally angled tip 1206 located at a distal end of the shaft 1204. The strike instrument 1201 further includes a strike pin 1215, and an impact surface 1228 located at one end of the strike pin 1215. In one embodiment, the strike instrument 1201 may include a slotted "female" complementary feature for engaging a T-shaped (or other similarly shaped) "male" engaging feature of the microfracture pick 1200. It is noted that the longitudinal axis 1232 of the strike pin 1215 may be parallel or non-parallel with respect to the direction 1233 of the tip 1206.

Figure 13:
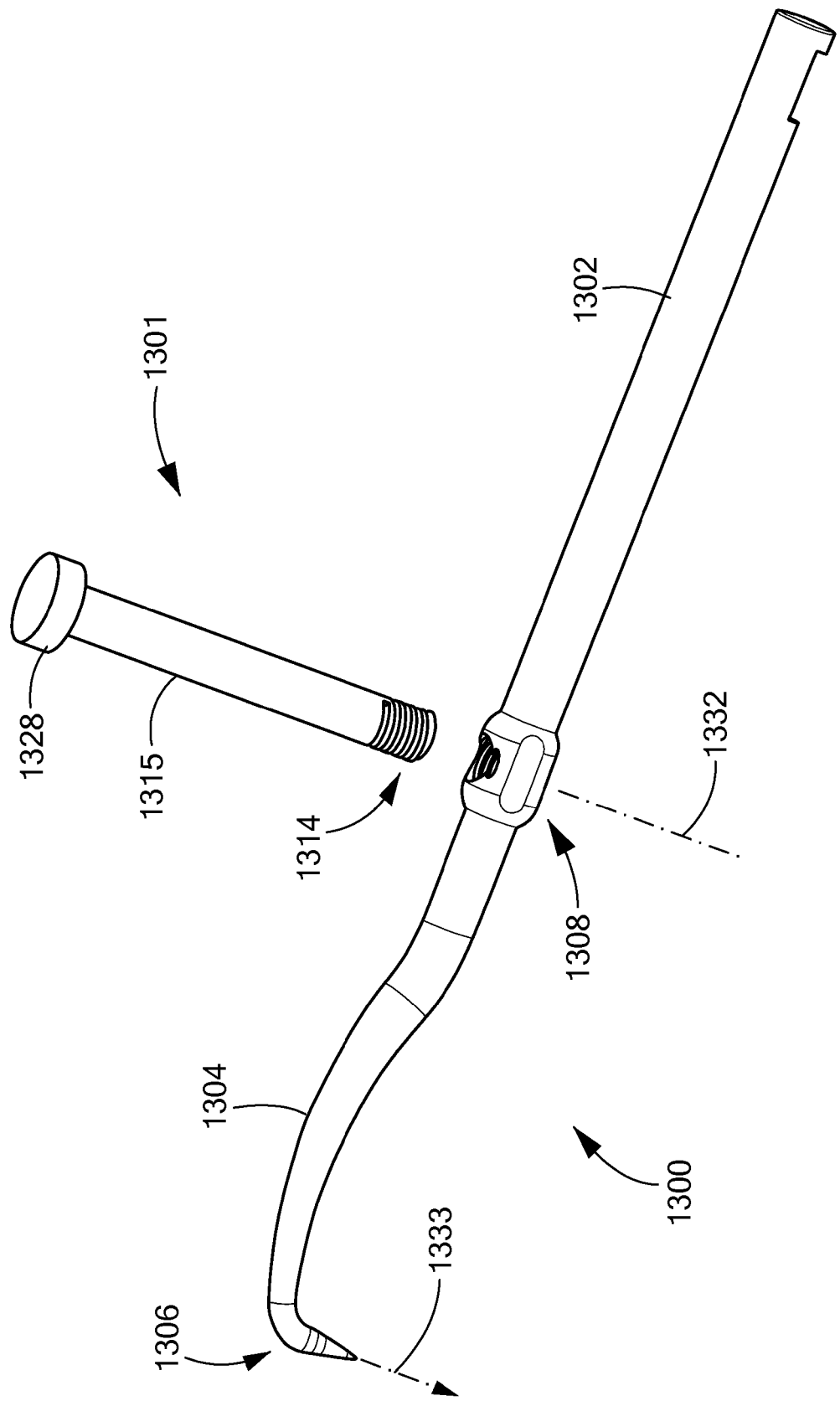

FIG. 13 depicts a strike instrument 1301 that includes a threaded "male" complementary feature 1314 for engaging a threaded "female" engaging feature 1308 of a microfracture pick 1300. The microfracture pick 1300 further includes a handle 1302, a shaft 1304, and an optionally angled tip 1306 located at a distal end of the shaft 1304. The strike instrument 1301 further includes a strike pin 1315, and an impact surface 1328 located at one end of the strike pin 1315. In one embodiment, the strike instrument 1301 may include a threaded "female" complementary feature for engaging a threaded "male" engaging feature of the microfracture pick 1300. For example, the threaded "male" complementary feature 1314 and the threaded "female" engaging feature 1308 may be configured to provide a quarter turn, luer lock, or any other suitable engagement. It is noted that the longitudinal axis 1332 of the strike pin 1315 may be parallel or non-parallel with respect to the direction 1333 of the tip 1306.

Figure 14:
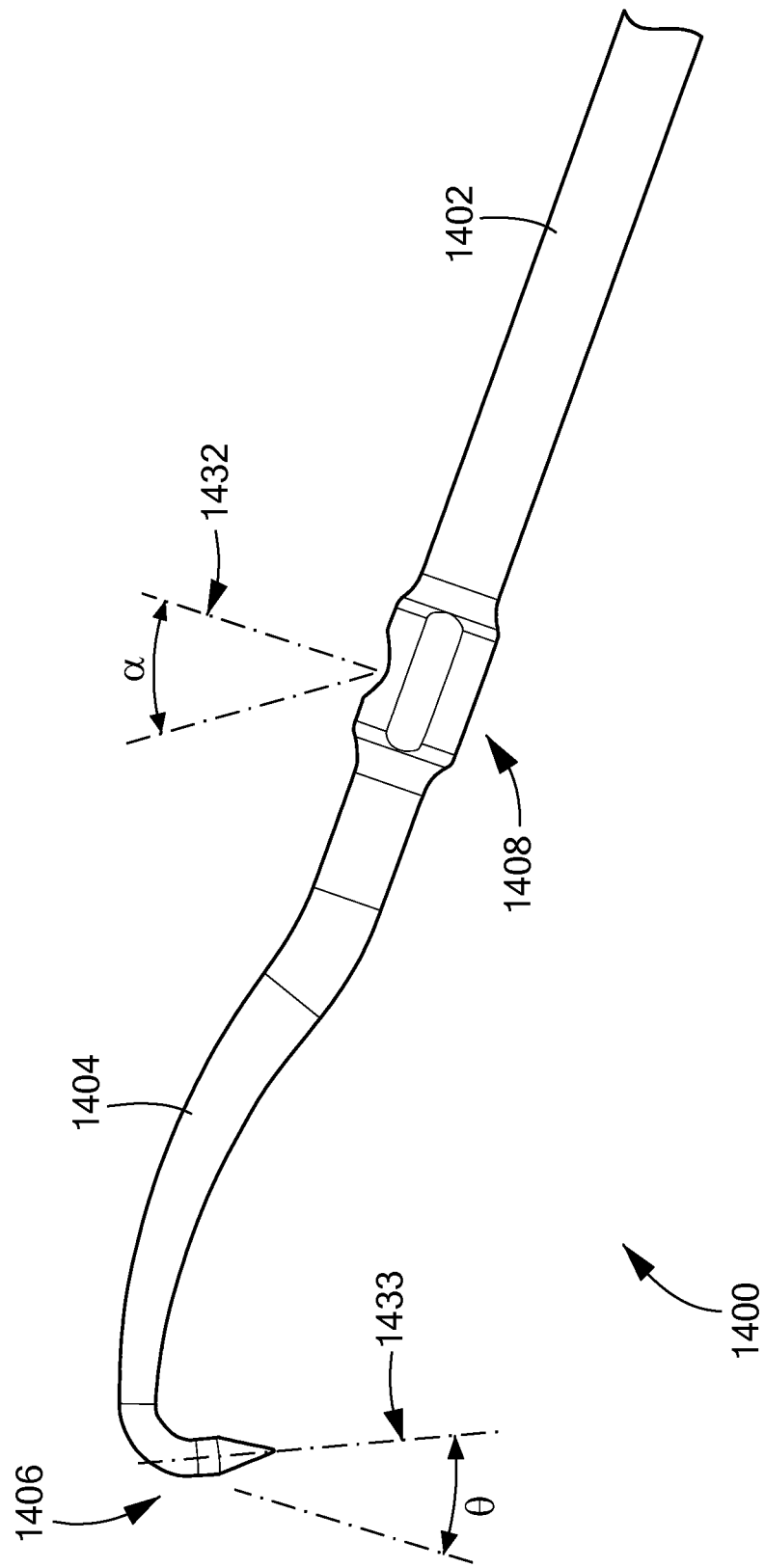

FIG. 14 depicts a microfracture pick 1400 that includes a handle 1402, a shaft 1404, an angled tip 1406 located at a distal end of the shaft 1404, and an engaging feature 1408 configured to engage a complementary feature (not shown) of a strike instrument. As shown in FIG. 14, the angle of the tip 1406 can vary within any suitable range of an angle θ. In one embodiment, the angle θ can be greater than 90°. Further, the strike instrument can engage the engaging feature 1408 at any suitable angle γ. Accordingly, the strike instrument can be used to generate a force along its longitudinal axis 1432, within a range of the angle γ, either parallel to the direction 1433 of the tip 1406 or non-parallel with respect to the tip 1406, thereby avoiding potential interference with a portion of a patient's anatomy.

FIG. 15a depicts a microfracture pick 1500 that includes a handle 1502, a shaft 1504, an angled tip 1506 located at a distal end of the shaft 1504, and an engaging feature 1508 configured to engage a complementary feature (not shown) of a strike instrument. As shown in FIGS. 15a and 15b, the angle of the tip 1506 can vary within any suitable range of an angle θ (see FIG. 15a), as well as within any suitable range of an angle $θ_a$ (FIG. 15b). Further, the strike instrument can engage the engaging feature 1508 at any suitable angle γ (see FIG. 15a), as well as any suitable angle $γ_a$ (see FIG. 15b). Accordingly, the strike instrument can be used to generate a force along its longitudinal axis 1532, within respective ranges of the angle γ and/or the angle $γ_a$, either parallel to the direction 1533 of the tip 1506 or non-parallel with respect to the tip 1506, thereby allowing improved access to various anatomies.

FIG. 16a depicts a microfracture pick 1600 that includes a handle 1602, a shaft 1604, an optionally angled tip 1606 located at a distal end of the shaft 1604, and an engaging feature 1608 configured to engage a complementary feature (not shown) of a strike instrument. FIG. 16b depicts a sectional view of the microfracture pick 1600 of FIG. 16a. As shown in FIGS. 16a and 16b, the engaging feature 1608 can be configured as a ball type feature that allows the complementary feature of the strike instrument, such as a ball swivel feature, to float or rotate within the ball type feature of the microfracture pick 1600. It is noted that the engaging feature 1608 configured as the ball type feature may not be entirely round, but may be partially rounded to limit the movement of the strike instrument in one or more directions. For example, the engaging feature 1608 may be disk shaped, or any other suitable rounded or partially rounded shape. In one embodiment, the complementary feature of the strike instrument may be configured as a ball type feature, and the engaging feature 1608 of the microfracture pick 1600 may be configured as a ball swivel feature.

FIG. 17a depicts a sectional view of a strike instrument 1701 that includes a complementary feature 1714 for engaging an engaging feature 1708 of a microfracture pick 1700. The microfracture pick 1700 further includes a handle 1702, a shaft 1704, and an optionally angled tip 1706 located at a distal end of the shaft 1704. The strike instrument 1701 further includes a strike pin 1715, and an impact surface 1791 located at one end of the strike pin 1715. The strike instrument 1701 is configured to engage with the microfracture pick 1700, and to be used in a reverse motion (as indicated by directional arrow 1795) to facilitate perforation of various anatomies. As shown in FIG. 17a, the strike instrument 1701 can include a slap hammer feature 1790 and/or the impact surface 1791 for striking with a mallet. As shown in FIG. 17b, the engaging feature 1708 can be configured to include a C-shaped opening for easy access.

Figure 18:
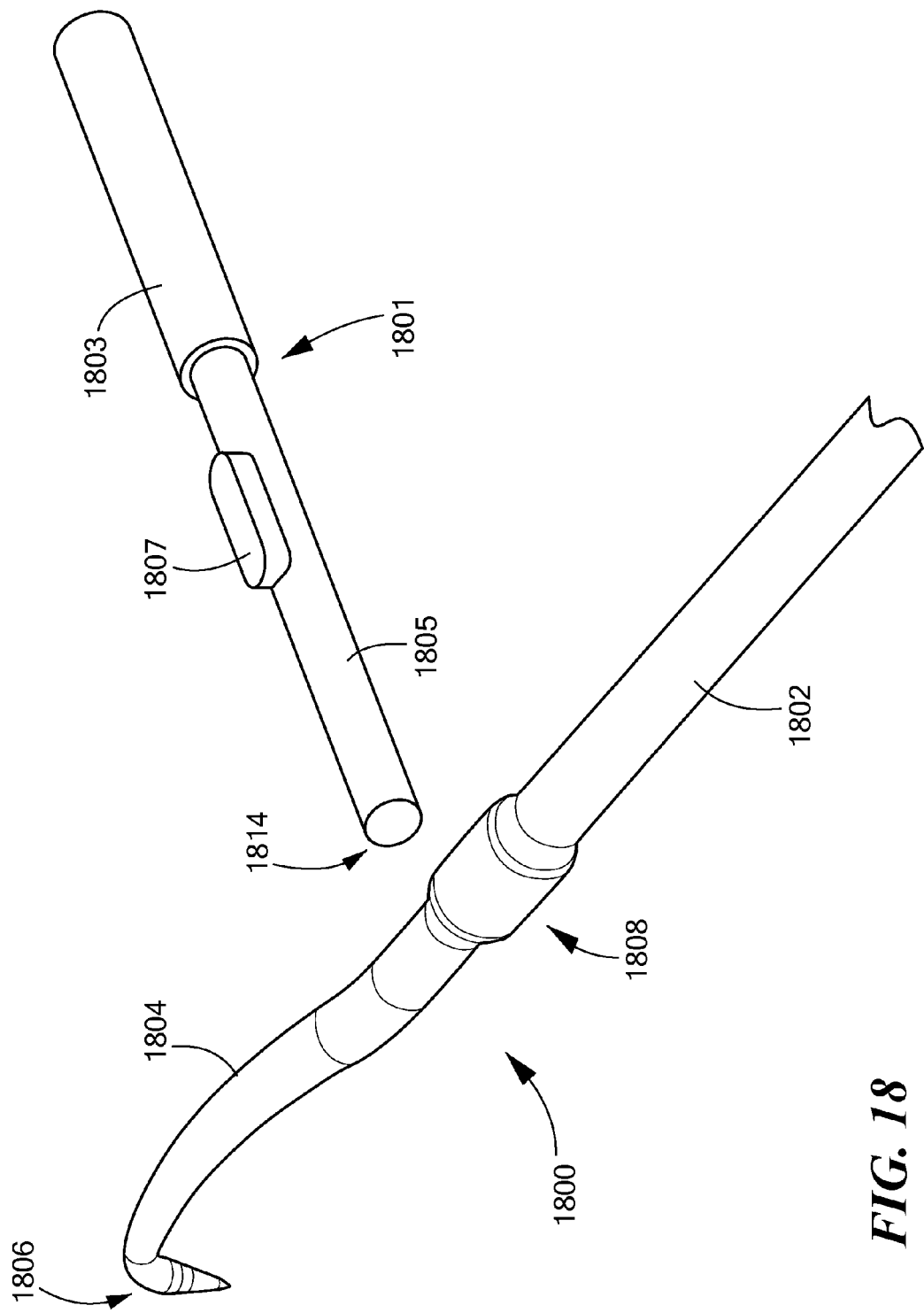

FIG. 18 depicts a strike instrument 1801 that includes a complementary feature 1814 suitably configured for engaging an engaging feature 1808 of a microfracture pick 1800. The microfracture pick 1800 further includes a handle 1802, a shaft 1804, and an optionally angled tip 1806 located at a distal end of the shaft 1804. The strike instrument 1801 further includes a handle 1803, a shaft 1805, and a strike zone 1807 located on the shaft 1805 for striking with a mallet. It is noted that the complementary feature 1814 of the strike instrument 1801 can be configured to engage with the engaging feature 1808 of the microfracture pick 1800 at any suitable angle.

Although the above illustrative embodiments of the disclosed microfracture pick have been described for use in the context of resurfacing cartilage surfaces, they can also be used for perforating the subchondral bone in the subtalar/talus space (ankle) in arthrodesis procedures. In such arthrodesis procedures, a surgeon typically removes the cartilage on both the subtalar bone and the talus bone, and uses the microfracture pick to perforate the subtalar and talus bones in multiple places to promote bleeding. A screw is then delivered between the subtalar and talus bones to fuse the two bones together.

It will be appreciated by those of ordinary skill in the art that further modifications to and variations of the above-described microfracture pick may be made without departing from the inventive concepts disclosed herein. Accordingly, the invention should not be viewed as limited except as by the scope and spirit of the appended claims.

What is claimed is:

1. A system for use in performing a microfracture procedure, comprising:
   a strike instrument including a first elongated member having a proximal end, a distal end, and a hole in the first elongated member near its distal end, a strike pin configured to pass through the hole in the first elongated member, and an impact surface located at one end of the strike pin; and
   a surgical device including a second elongated member having a distal end, an engaging feature located on the second elongated member, and a tip disposed adjacent the distal end of the second elongated member, wherein the strike instrument further includes a complementary feature located at another end of the strike pin, wherein the engaging feature of the surgical device is operative to engage the complementary feature of the strike instrument, and wherein the first elongated member is configured to be disposed generally parallel to a longitudinal axis of the surgical device to allow engagement of the engaging feature with the complementary feature, whereby, upon striking the impact surface of the strike instrument, a three is produced that is translated via the second elongated member through the tip.

2. The system of claim 1 wherein the first elongated member is configured to be at least temporarily fixated to the surgical device.

3. The system of claim 1 wherein the engaging feature of the surgical device is configured as a female connector, and the complementary feature of the strike instrument is configured as a male connector.

4. The system of claim 1 wherein the engaging feature of the surgical device is configured as a male connector, and the complementary feature of the strike instrument is configured as a female connector.

* * * * *